United States Patent
Young et al.

(10) Patent No.: US 9,427,533 B2
(45) Date of Patent: Aug. 30, 2016

(54) MEDICATED MODULE FOR AN INHALER

(75) Inventors: Alasdair George Young, Warwickshire (GB); Daniel Thomas De Sausmarez Lintell, Warwickshire (GB); David Richard Mercer, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 371 days.

(21) Appl. No.: 13/988,780

(22) PCT Filed: Nov. 28, 2011

(86) PCT No.: PCT/EP2011/071120
§ 371 (c)(1),
(2), (4) Date: May 22, 2013

(87) PCT Pub. No.: WO2012/072544
PCT Pub. Date: Jun. 7, 2012

(65) Prior Publication Data
US 2013/0233313 A1    Sep. 12, 2013

Related U.S. Application Data

(60) Provisional application No. 61/433,705, filed on Jan. 18, 2011.

(30) Foreign Application Priority Data

Nov. 29, 2010  (EP) .................... 10192977

(51) Int. Cl.
*A61M 16/00* (2006.01)
*A61M 15/00* (2006.01)
*A61M 31/00* (2006.01)

(52) U.S. Cl.
CPC ..... *A61M 15/0028* (2013.01); *A61M 15/0003* (2014.02); *A61M 15/0021* (2014.02);

(Continued)

(58) Field of Classification Search
CPC ...... A61M 1/00; A61M 11/00; A61M 13/00; A61M 11/02; A61M 15/00; A61M 15/0028; A61M 15/003; A61M 15/0031; A61M 15/0032; A61M 15/0033; A61M 15/0038; A61M 15/004
See application file for complete search history.

(56) References Cited

U.S. PATENT DOCUMENTS 5,201,308 A * 4/1993 Newhouse ........ A61M 15/0065
                                                         128/203.15
5,301,666 A * 4/1994 Lerk .................. A61M 15/005
                                                         128/203.15

(Continued)

FOREIGN PATENT DOCUMENTS

GB    2420982 A    6/2006
GB    2439204 A    12/2007

(Continued)

OTHER PUBLICATIONS

English Translation of Notice of Reasons for Rejection issued in Japanese Patent Application No. 2013-540394 dated Sep. 29, 2015.

*Primary Examiner* — Jason Flick
*Assistant Examiner* — Victoria Leszczak
(74) *Attorney, Agent, or Firm* — McDonnell Boehnen Hulbert & Berghoff LLP

(57) ABSTRACT

A medicated module containing a second medicament is configured for removable attachment to the mouthpiece of an inhaler containing a first medicament such that a single inhalation by a user will deliver both medicaments to the user.

10 Claims, 2 Drawing Sheets

(52) U.S. Cl.
CPC ..... *A61M15/0031* (2014.02); *A61M 15/0043* (2014.02); *A61M 15/0045* (2013.01); *A61M 31/00* (2013.01); *A61M 2202/064* (2013.01)

(56) References Cited

U.S. PATENT DOCUMENTS

| | | | | |
|---|---|---|---|---|
| 5,349,947 | A * | 9/1994 | Newhouse | A61M 15/0028 128/203.15 |
| 5,492,112 | A * | 2/1996 | Mecikalski | A61K 9/0075 128/203.15 |
| 5,752,505 | A * | 5/1998 | Ohki | A61M 15/0028 128/203.15 |
| 5,823,183 | A * | 10/1998 | Casper | A61M 15/0028 128/200.24 |
| 6,401,712 | B1 * | 6/2002 | von Schuckmann | A61J 1/035 128/203.12 |
| 6,715,486 | B2 * | 4/2004 | Gieschen | A61M 15/0086 128/203.12 |
| 6,752,148 | B1 * | 6/2004 | McGinn | A61M 15/0045 128/203.15 |
| 7,163,013 | B2 * | 1/2007 | Harrison | A61M 15/0028 128/203.15 |
| 2002/0092524 | A1 * | 7/2002 | Lockhart | A61M 15/0028 128/203.21 |
| 2002/0121276 | A1 * | 9/2002 | Genova | A61M 15/0086 128/200.23 |
| 2003/0094173 | A1 * | 5/2003 | Burr | A61M 15/0028 128/200.23 |
| 2003/0199832 | A1 * | 10/2003 | Greiner-Perth | A61M 15/0028 604/190 |
| 2003/0209245 | A1 * | 11/2003 | Poole | A61M 15/0028 128/203.15 |
| 2004/0011356 | A1 * | 1/2004 | Sullivan | A61M 15/0028 128/200.14 |
| 2004/0118399 | A1 * | 6/2004 | Young | A61M 15/0008 128/203.15 |
| 2004/0182387 | A1 * | 9/2004 | Steiner | A61M 15/0028 128/203.15 |
| 2004/0206773 | A1 * | 10/2004 | Ede | A61J 1/035 222/83 |
| 2005/0252511 | A1 * | 11/2005 | Pentafragas | A61M 15/0028 128/203.15 |
| 2007/0181124 | A1 * | 8/2007 | Casper | A61M 15/0045 128/203.15 |
| 2008/0314384 | A1 * | 12/2008 | Harris | A61M 15/0028 128/203.15 |
| 2009/0293873 | A1 * | 12/2009 | Djupesland | A61M 15/0028 128/203.15 |
| 2010/0000531 | A1 | 1/2010 | Smith et al. | |
| 2010/0024834 | A1 * | 2/2010 | Oglesby | A24F 47/006 131/194 |

FOREIGN PATENT DOCUMENTS

| | | |
|---|---|---|
| WO | 0236189 A1 | 5/2002 |
| WO | 2004011071 A1 | 2/2004 |
| WO | 2005089843 A1 | 9/2005 |

\* cited by examiner

MEDICATED MODULE FOR AN INHALER

CROSS REFERENCE TO RELATED APPLICATIONS

The present application is a U.S. National Phase Application pursuant to 35 U.S.C. §371 of International Application No. PCT/EP2011/071120 filed Nov. 28, 2011, which claims priority to European Patent Application No. 10192977.6 filed Nov. 29, 2010 and U.S. Provisional Patent Application No. 61/433,705 filed Jan. 18, 2011. The entire disclosure contents of these applications are herewith incorporated by reference into the present application.

FIELD OF INVENTION

The present application relates in one embodiment to medical devices and methods of delivering at least two drug agents from separate reservoirs or containers using inhaler devices that are configured for a single user inhalation through a single dispense interface (i.e., a mouthpiece). A delivery procedure initiated by the user causes a non-user settable dose (i.e., a fixed dose) of a second drug agent along with a set dose of a first drug agent to be delivered to the patient. The drug agents may be available in two or more reservoirs, containers, or packages, each containing independent (single drug compound) or pre-mixed (co-formulated multiple drug compounds) drug agents. Other embodiments relate to delivering one drug agent.

BACKGROUND

Certain disease states require treatment using one or more different medicaments. Some drug compounds need to be delivered in a specific relationship with each other in order to deliver the optimum therapeutic dose. This invention is of particular benefit where combination therapy is desirable, but not possible in a single formulation for reasons such as, but not limited to, stability, compromised therapeutic performance, and/or toxicology.

For example, in some cases it might be beneficial to treat a person suffering from diabetes with a combination of a long acting insulin along with a glucagon-like peptide-1 (GLP-1). This GLP-1 is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus. Alternatively, other combination of drugs such as those to treat asthma, e.g., LABA (Long acting beta agonists) and Cortico-steroids could be used in this invention.

A number of potential problems can arise when delivering two active medicaments or "agents" simultaneously. As just one example, the two active agents when present in a single container may interact with each other during the long-term, shelf life storage of the formulation. Therefore, there are certain advantages to storing the active components separately and then potentially combine them at the point of delivery, e.g. injection, needle-less injection, pumps, or inhalation. However, any potential process for combining the two or more agents needs to be straightforward and convenient for the user to perform reliably, repeatedly, and safely.

One further concern is that the quantities and/or proportions of each active agent making up the potential combination dose or therapy may need to be varied for each user or at different stages of their therapy. Again, as just one example, one or more active agents may require a titration period to gradually introduce a patient to a "maintenance" dose. A further example would be if one active agent requires a non-adjustable fixed dose while the other agent is varied in response to a patient's symptoms or physical condition. This potential concern could mean that pre-mixed formulations of multiple active agents may not be suitable as these pre-mixed formulations would have a fixed ratio of the active components, which could not be varied by the healthcare professional or user.

Additional concerns may arise where a multi-drug compound therapy is required, because certain users may not be able to cope with having to use more than one drug delivery system or make the necessary accurate calculation of the required dose combination. This is especially true for users with dexterity or computational difficulties.

Accordingly, there exists a strong need to provide devices and methods for the delivery of two or more medicaments in a single activation of an inhaler-type drug delivery device, such as a dry powder inhaler that is simple and safe for the user to perform and that also tends to reduce a patient's anxiety towards taking repeated doses of medicaments.

SUMMARY

The present application discloses a medicated module attachable to an inhaler device, preferably a dry powder inhaler (DPI), to provide a means of delivering one or more pre-determined doses of a secondary inhaled medication automatically during a patient's inspiratory air flow through the inhaler device, which contains one or more doses of a primary or first medicament. Such dry powder inhalation systems, which combines a standard multi-use DPI device, such as a "Disk-haler" containing a primary medicament (such as a Bronchodilator) with a single-use medicated module containing a secondary medicament (such as a corticosteroid) provides a means by which the user/patient receives a combination dose of at least two medicaments during a single inhalation, thus reducing their burden on storage and complexity of operation etc.

Alternatively, the medicated module could be used with an inhaler that does not contain a first medicament, e.g. an inhaler from which all medicament has been dispensed. In this case the secondary medicament of the module would be the only medicament in the inhaler drug delivery system comprising the inhaler device and the medicated module.

Accordingly, an inhaler drug delivery system according to the present invention comprises, in combination, a medicated module according to the present invention and a dry powder inhaler housing. In one embodiment the dry powder inhaler housing may further comprise a reservoir of a powdered medicament.

The medicated module seeks to maintain the delivered dose performance (e.e. Fine Particle Fraction, FPF or Fine Particle Mass, FPM) of the primary device by ensuring that the design of the flow geometry of the medicated module does not compromise the airflow-induced de-aggregation forces generated within the primary DPI device. Careful selection of the geometries within the medicated module housing will minimize the potential for significant changes to airflow resistance (AFR) of the system, while also reducing, as far as is practicable, opportunities for powder deposition within the airflow path. The intention is that doing this should help to ensure good comparability between the delivered dose performance of the primary medicament from the primary device when used in isolation, as well as when it is used in combination with the medicated module.

The medicated module of this invention provides a means of containing the second medicament within a drug cavity located in the housing of the medicated module. Preferably, the second medicament is a single dose that is contained with a primary pack or container, such as, most preferably a single cavity blister of the type known in the art. Such blisters may be manufactured from cold-formed sheet or strip materials and may be either made from single material type, or multi-layer materials (plastic (e.g. PVC) and aluminum laminate). The blister pocket that contains the second medicament would be hermetically sealed by an upper foil (or similar) and preferably configured to be either peelably attached to the base foil or configured to facilitate controlled rupturing when acted upon by up-stand features (or similar) that might be present in the blister cavity, for example compressive forces. Both means of accessing the dry powder formulation contained in the blister are known in the art. Alternative forms of the blister, such as injection molded cavities in plastic (e.g. POM, COC, PBT, COP or a combination) are also possible.

One advantage of the proposed systems is that the secondary medicament is automatically introduced into the airflow path upon attachment of the medicated module to a standard inhaler. Preferably, the connection between the mouthpiece of the primary inhaler device and the inlet port of the medicated module will be configured to help ensure minimal bypass airflow occurs at this joint during inhalation, thus helping to maintain delivered dose performance and minimize potential AFR variability.

The system may also be configured to help ensure that the medicated module is only capable of being used once by a user. This may be achieved through integration of a mechanical flap (or similar airflow restriction means) that is only activated (closed off) following an inhalation by a user through the device. The aim of any such mechanism or feature would be to prevent/significantly restrict subsequent further airflow through the medicated module, thereby alerting a user to this situation. Alternatively and/or additionally our invention could include features to;

1. Prevent re-attachment of a previously used medicated module to the primary drug delivery device.

2. Visual warnings (e.g. warning text/indicia within an indication window on the module once the blister has been opened.

Prior to use, i.e., attachment to an inhaler, the medicated module provides a means of containing the second medicament within a sealed drug cavity or reservoir. Potential materials that might be used to form the drug cavity that holds the second medicament might include (but are not limited to); Acetal (polyoxymethylene, polyacetal or polyformaldehyde), COC (Cyclo Olefin Copolymer), COP (Cyclo Olefin Polymer) and PBT (Polybutylene Terephthalate). Sealing of the reservoir in the medicated module may be achieved through a combination of foil seals (single or multi-layer), stopper bungs, septa or like means known in the art.

On assembly to the primary device, the container of second medicament in the medicated module is automatically engaged (i.e., opened) thus exposing the medicament to air flow scouring or depositing the second medicament into a de-aggregation chamber that is in the flow path to the outlet orifice, i.e., mouthpiece, at the distal end of the medicated module. Preferably, connections in the flow path could be established using a compliant material, such as rubber or TPE, to help ensure minimal or no leakage occurs during dispense and thus delivered dose performance is maintained. The act of engaging the fluid flow path of the medicated module with that of the first medicament in the inhaler automatically during assembly simplifies the users interaction with the device.

In one embodiment of the invention the medicated module for use with a drug inhaler includes a housing configured for removable attachment to the mouthpiece of the inhaler, where the housing has a distal end and a proximal end. There is at least one medicament container contained within the housing containing at least one dose of a second medicament. The medicated module can also have a sliding member that opens the container when the medicated module is attached to an inhaler. Alternatively, the sliding member opens the container by compression when the container is moved relative to an outer housing portion of the medicated module. Most preferably, the container is a blister.

In yet another embodiment, the invention comprises a system of one or more of the previously described medicated modules in combination with a dry powder inhaler containing a primary medicament.

In one embodiment of the invention the medicated module may comprise a flow path extending between a first opening and a second opening. In one embodiment the de-aggregation chamber may be in fluid communication with the flow path. In another embodiment the first opening may be configured as an outlet orifice, e.g. a mouthpiece of the module. In another embodiment the second opening may be configured to provide fluid communication between the flow path and the inhaler.

In a preferred embodiment a master drug compound, such as insulin, contained within a multiple dose, user-selectable device could be used with a single use, user-replaceable, module that contains a single dose of a secondary medicament and the single dispense interface. When connected to the drug delivery device the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro (B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(w-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

The term "drug" or "medicament", as used herein, means a pharmaceutical formulation containing at least one pharmaceutically active compound, for example for the treatment of obstructive airway or lung diseases such as asthma or chronic obstructive pulmonary disease (COPD), allergies, diabetes mellitus.

The active pharmaceutical compound is preferably selected from the group consisting of active pharmaceutical compounds suitable for inhalation, preferably antiallergenic, antihistamine, anti-inflammatory, antitussive agents, bronchodilators, anticholinergic drugs, and combinations thereof.

The active pharmaceutical compound may for example be chosen from:

an insulin such as human insulin, e.g. a recombinant human insulin, or a human insulin analogue or derivative, a glucagon-like peptide (GLP-1) or an analogue or derivative thereof, or exendin-3 or exendin-4 or an analogue or derivative of exendin-3 or exendin-4;

an adrenergic agent such as a short acting β2-agonists (e.g. Salbutamol, Albuterol, Levosalbutamol, Fenoterol, Terbutaline, Pirbuterol, Procaterol, Bitolterol, Rimiterol, Carbuterol, Tulobuterol, Reproterol), a long acting β2-agonist (LABA, e.g. Arformoterol, Bambuterol, Clenbuterol, Formoterol, Salmeterol), an ultra LABA (e.g. Indacaterol) or another adrenergic agent (e.g. Epinephrine, Hexoprenaline, Isoprenaline (Isoproterenol), Orciprenaline (Metaproterenol));

a glucocorticoid (e.g. Beclometasone, Budesonide, Ciclesonide, Fluticasone, Mometasone, Flunisolide, Betamethasone, Triamcinolone);

an anticholinergic agent or muscarinic antagonist (e.g. Ipratropium bromide, Oxitropium bromide, Tiotropium bromide);

a mast cell stabilizer (e.g. Cromoglicate, Nedocromil);

a xanthine derivative (e.g. Doxofylline, Enprofylline, Theobromine, Theophylline, Aminophylline, Choline theophyllinate);

an eicosanoid inhibitor, such as a leukotriene antagonist (e.g. Montelukast, Pranlukast, Zafirlukast), a lipoxygenase inhibitor (e.g. Zileuton) or a thromboxane receptor antagonist (e.g. Ramatroban, Seratrodast);

or a combination of any two, three or more of the above-mentioned compound classes or compounds (e.g. Budesonide/Formoterol, Fluticasone/Salmeterol, Ipratropium bromide/Salbutamol, Mometasone/Formoterol);

or a pharmaceutically acceptable salt or solvate or esters of any of the above named compounds.

Pharmaceutically acceptable salts are for example acid addition salts and basic salts. Acid addition salts are e.g. a chloride, bromide, iodide, nitrate, carbonate, sulfate, methylsulfate, phosphate, acetate, benzoate, benzenesulfonate, fumarate, malonate, tartrate, succinate, citrate, lactate, gluconate, glutamate, edetate, mesylate, pamoate, pantothenate or a hydroxy-naphthoate salt. Basic salts are for example salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology. Pharmaceutically acceptable ester may for example be acetates, propionates, phosphates, succinates or etabonates.

Pharmaceutically acceptable solvates are for example hydrates.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
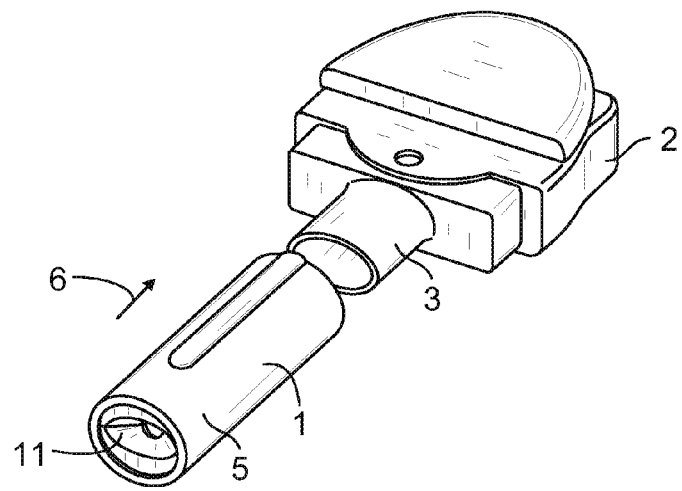
FIG. 1 illustrates a perspective view of one possible drug delivery system of the present invention where a medicated module according to the present invention is shown being attached to the mouthpiece of an inhaler.

The presently proposed medicated module may be used with an inhaler-type drug delivery device, such as the inhaler 2 illustrated in FIG. 1. In one arrangement, the presently proposed medicated module administers one or more single doses of a second medicament simultaneously with a fixed dose of a first medicament from a multi-dose reservoir or blister pack within the inhaler through a single output or drug dispense interface, such as module mouthpiece 11. A single activation of inhaler 2, for example by inhalation of a user, will cause both the first and second medicaments to be administered to the user. The volume and size of the dose of the second medicament is independently controlled by the design and manufacture of the reservoir, container, drug cavity, blister, etc. in the medicated module and therefore not influenced by the size of the dose generated by the inhaler during activation. This fixed dose of the second medicament contained within the medicated module may be a single dose.

In a preferred arrangement, the drug dispense interface comprises a module mouthpiece, such as the mouthpiece 11 shown in FIGS. 1-5, however, any channel or flow path capable of passing a stream of dry powder could be used. As shown in FIG. 1, the medicated module 1 comprising a housing 5 that is preferably designed and configured to be removably attached in direction 6 to a standard inhaler 2. A preferred attachment is one where the housing 5 of the medicated module 1 can be inserted over the mouthpiece 3 of the inhaler 2. The housing 5 is held in place using any reversible connection means known to the art, for example, threads, snap locks, snap fits, detents, luer locks, bayonet, snap rings, keyed slots, and combinations of such connections. Preferably, the attachment mechanism between the medicated module and the inhaler is configured such that the user can easily attach the module to the inhaler and then easily remove the module after expelling the second medicament contained in the module. In certain applications, the connector or attachment configuration may comprise an exclusive attachment where such an exclusive attachment would only allow such a medicated module to be attached to only certain types of inhaler drug delivery devices and prevented from being attached to other types of inhalers or other drug delivery devices. Once the module is removed, the inhaler can then be used as a stand-alone drug delivery device to administer the first or primary medicament.

Figure 2:
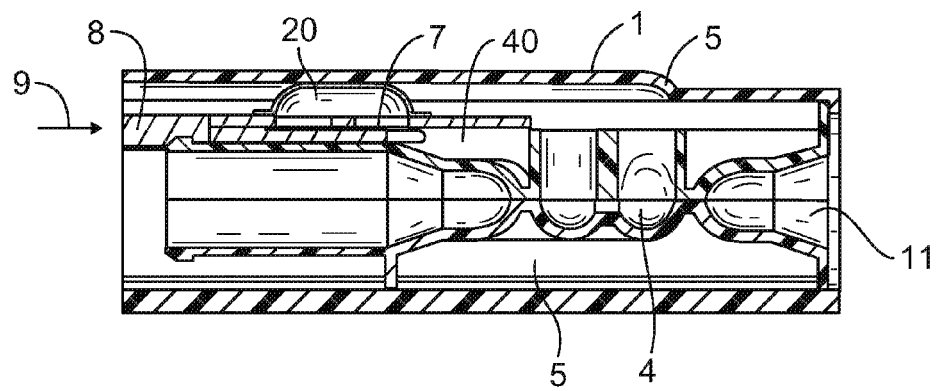
FIG. 2 illustrates a sectional view of one arrangement of a medicated module prior to being attached to an inhaler.
Figure 3:
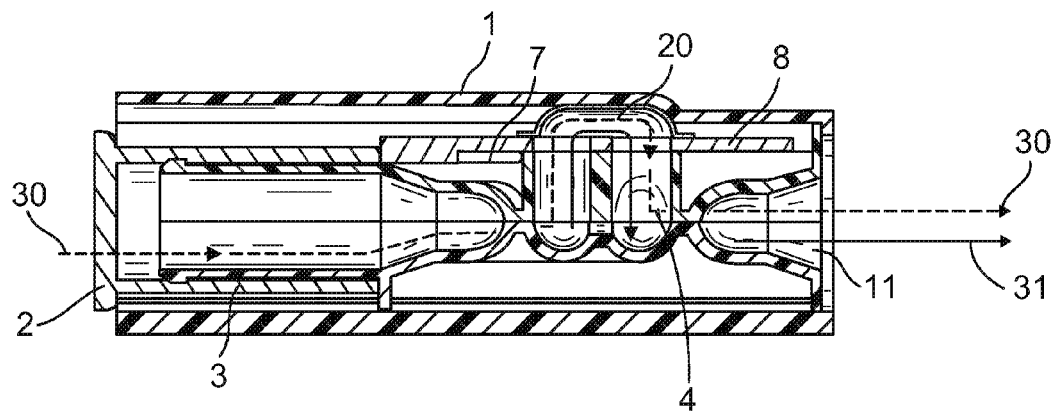
FIG. 3 illustrates a sectional view of the medicated module illustrated in FIG. 2 after complete attachment to the mouthpiece of the inhaler.

The inhaler device 2 shown in FIG. 1 is a dry powder inhaler (DPI) that generally contains multiple doses of the first medicament, typically in a blister pack arrangement. Although a specific design of a PDI is illustrated, other types of DPI might also be suitable for use with the present invention. Alternatively, the medicated module could be used with an inhaler that does not contain a first medicament, e.g. an inhaler from which all medicament has been dispensed. In this case the second medicament of the module according to the description would be the only medicament in the inhaler drug delivery system. Referring now to FIGS. 2 and 3, these figures show a close-up view of the cross-sectional view of one embodiment of the medicated module 1. FIG. 2 shows the module before fully attaching it to the inhaler 2, where the container 20, shown as a blister, contains the second medicament and is sealed with seal 7. Seal 7 is also attached to housing 5. Housing 5 has a sliding member 8 that is connected to container 20 and moves in direction 9 when the module 1 is fully attached to the mouthpiece 3 of inhaler 2.

FIG. 3 shows the module 1 attached to inhaler 2. The sliding member 8 and container 20 have moved distally such that the container 20 is positioned over the de-aggregation chamber 4. As sliding member 8 and container 20 are moved, seal 7 is peeled or torn away from the under side of the container immediately before being positioned over the de-aggregation chamber 4. The medicament preferably stays contained in container 20 due to the cohesive forces produced by the compaction of the medicament during filling of the container. The user operates the combination of medicated module 1 and inhaler 2 in exactly the same manner as they would if the module was not attached. Having successfully completed any set-up operations for the primary device (such as actuation of a priming level), when the user inhales on mouthpiece 11 of the medicated module 1, airflow with entrained powdered first medicament is drawn through inhaler mouthpiece 3, through housing 5, then through de-aggregation chamber 4 where the second medicament has also been entrained as flow 31, and the flow mix of the two medicaments, 30 and 31, is then inhaled through medicated module mouthpiece 11 and administered to the user. The secondary medicament will start to be entrained as soon as air begins to flow from the primary device arrives at the container.

In one preferred arrangement, the container or blister 20 comprises a single dose of the second medicament, such as a single dose of an active agent such as GLP-1. Alternatively, the reservoir comprises a single dose of a premix of active agents or medicaments. In one preferred arrangement, this primary medicament comprises a different type of medicament as the medicament contained within the drug delivery device.

Figure 4:
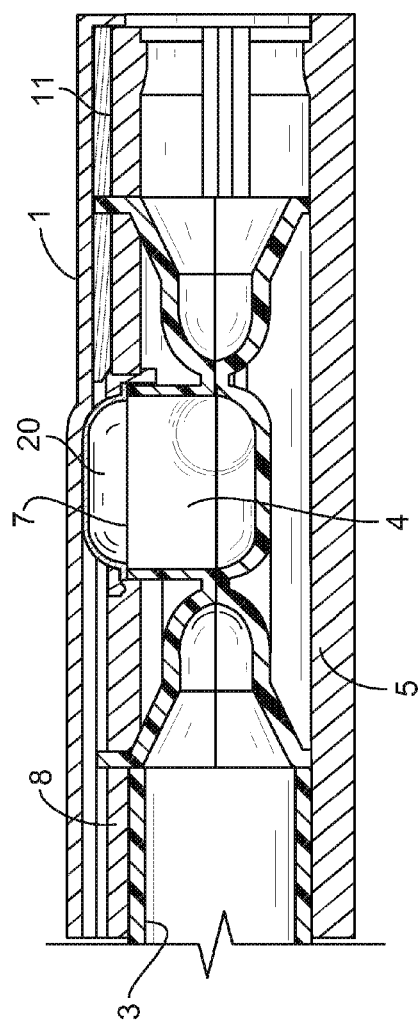
FIG. 4 illustrates a sectional view of another variation of the medicated module of this invention prior attachment to the mouthpiece of the inhaler.
Figure 5:
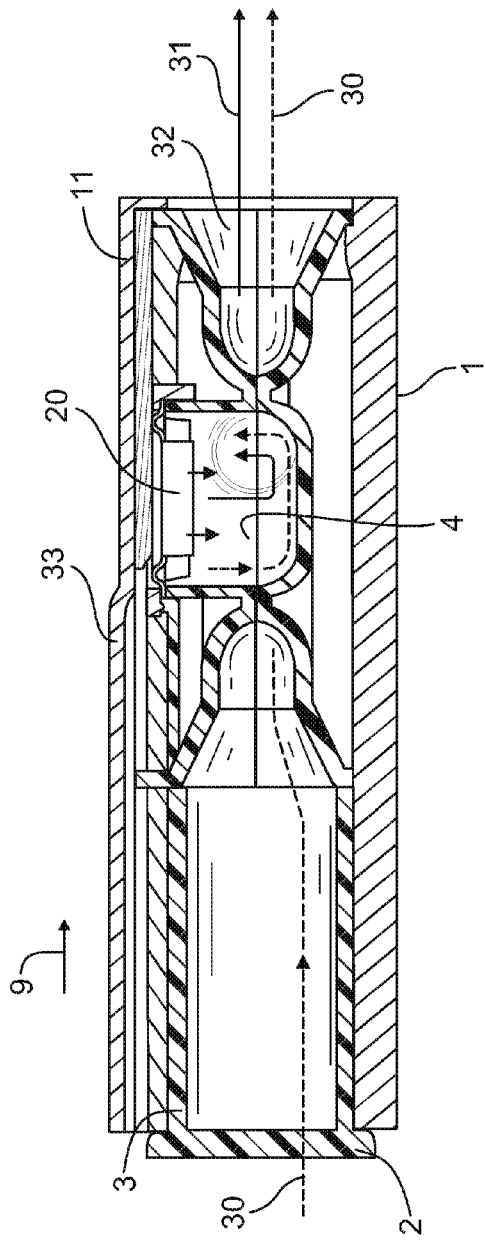
FIG. 5 illustrates a sectional view of the medicated module of FIG. 4 after attachment to an inhaler.

FIGS. 4 and 5 illustrate another possible embodiment of the medicated module of this invention where the container 20 is a compressible container, such as a blister, that is configured to be opened when compressed. FIG. 4 illustrates the medicated module 1 before attachment to inhaler 2. Container 20 is sealed along at least one face with seal 7. A sliding portion 8 of the housing 5 is moved in direction 9 when the medicated module is attached to the inhaler 2. This sliding portion 8 carries with it container 20, de-aggregation chamber 4, and internal flow channel 32. As the container 20 is moved distally it becomes compressed due to the narrowing of the outer portion 33 of housing 5. Because the relative positioning of container 20 and de-aggregation chamber 4 is fixed, the compression and opening of container 20 will cause the second medicament to drop into chamber 4.

As with the above-described embodiment, the user operates the combination of medicated module 1 and inhaler 2 in exactly the same manner as they would if the module was not attached. Having successfully completed any set-up operations for the primary device (such as actuation of a priming level), when the user inhales on mouthpiece 11 of the medicated module 1 air flow with entrained powdered first medicament is drawn through inhaler mouthpiece 2, through housing 5, then through de-aggregation chamber 4 where the second medicament has also been entrained, flow 31, and the flow of the two medicaments, 30 and 31, is then inhaled through medicated module mouthpiece 11 and administered to the user.

It is within the scope of the invention to configure the medicated module with a locking mechanism so as to lock and/or block the distal end, proximal end, or both after dose administration. One advantage of locking the medicated module from repeated use is that a user will be prevented from reusing an expended medicated module and therefore eliminate the possibility that a user would use the expended medicated module under the assumption that he or she is receiving the predefined dose of the primary medicament stored in a new medicated module. Likewise, such a blocking/locking feature prevents a user from re-using a non-sterile medicated module after a dose has been delivered.

The medicated module arrangements herein disclosed are preferably self-contained and may be provided as a sealed and sterile disposable module. Although not shown, the medicated modules disclosed herein could be supplied by a manufacturer contained in a protective and sterile capsule or container where the user would peel or rip open a seal or the container itself to gain access to the sterile medicated module. In some instances it might be desirable to provide two or more seals for each end of the medicated module.

Moreover, in the arrangements discussed above, these arrangements have the benefit in that the second medicament is contained entirely within the medicated module, separate and away from the first medicament contained within the inhaler-type drug delivery device.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module configured for use with a drug inhaler containing a first medicament, the medicated module comprising:
   a housing configured for attachment to the drug inhaler, where the housing has a distal end with a first opening and a proximal end with a second opening and a flow path extending between the first opening and the second opening;
   a medicament container containing a dose of a second medicament; a seal attached to the housing to prevent the second medicament from entering the flow path;
   a de-aggregation chamber configured to accept the second medicament from the medicament container upon opening the seal of the medicament container; and
   a sliding member connected to the medicament container;
   wherein the medicated module is configured such that attachment to the drug inhaler causes the sliding member to move in a distal direction such that the medicament container moves from a first position to a second position,
   wherein the second position is closer to the second opening than the first position, and
   wherein the movement of the container from the first position to the second position causes the seal to break, thereby opening the medicament container to the flow path, such that the first opening and the second opening are in fluid communication with the first medicament and the second medicament.

2. The medicated module of claim 1 where the medicament container and de-aggregation chamber are in fluid communication when the medicated module is in an attached state.

3. The medicated module of claim 1 where the medicament container is opened by the sliding member compressing the container against an inner portion of the housing.

4. The medicated module of claim 1 where the medicament container is a blister.

5. The medicated module of claim 1 where the de-aggregation chamber is in fluid communication with a mouthpiece of the drug inhaler when the medicated module is attached.

6. The medicated module of claim 1 wherein the de-aggregation chamber is in fluid communication with the flow path.

7. The medicated module of claim 1 wherein the first opening is configured as an outlet orifice, e.g. a mouthpiece of the module.

8. The medicated module of claim 1 wherein the second opening is configured to provide fluid communication between the flow path and the drug inhaler.

9. An inhaler drug delivery system comprising, in combination, the medicated module of claim 1; and a dry powder inhaler housing.

10. The inhaler drug delivery system according to claims 9, wherein the dry powder inhaler housing further comprises a reservoir of the first medicament in the form of a powdered medicament.

* * * * *